United States Patent [19]

Testa

[11] Patent Number: 4,797,422
[45] Date of Patent: Jan. 10, 1989

[54] PHARMACEUTICAL COMPOUNDS EFFECTIVE AGAINST SEVERAL DISORDERS OF THE EYE IN PARTICULAR THE CATARACT AND COMPOSITION CONTAINING THEM

[76] Inventor: Michele Testa, 30 Via Guantai Nuovi, 80133 Naples, Italy

[21] Appl. No.: 888,348

[22] Filed: Jul. 23, 1986

[30] Foreign Application Priority Data

Aug. 5, 1985 [IT] Italy .............................. 48447 A/85
Oct. 23, 1985 [IT] Italy .............................. 22596 A/85

[51] Int. Cl.$^4$ ............................................ A61K 31/045
[52] U.S. Cl. ............................................ 514/912; 514/724; 568/715
[58] Field of Search ................. 568/764, 715, 704; 514/724, 912, 420

[56] References Cited

U.S. PATENT DOCUMENTS

| | | | |
|---|---|---|---|
| 2,222,976 | 11/1940 | Fox . | |
| 2,631,169 | 3/1953 | Chiddix et al. | 568/764 |
| 3,037,057 | 5/1962 | Tinsley et al. | 568/715 |
| 3,679,804 | 7/1972 | Grunwaldt | 424/308 |
| 4,087,538 | 5/1978 | Portnoff | 424/274 |
| 4,136,178 | 1/1979 | Lin et al. | 424/211 |
| 4,192,959 | 3/1980 | Bauer et al. | 568/764 |
| 4,198,522 | 4/1980 | Shepherd | 424/199 |
| 4,283,565 | 8/1981 | Bernhardt et al. | 568/715 |
| 4,291,178 | 9/1981 | Ludec | 568/764 |
| 4,351,826 | 9/1982 | Clark et al. | 424/81 |
| 4,460,799 | 7/1984 | Perrin et al. | 568/764 |
| 4,615,877 | 10/1986 | Testa | 424/2 |

FOREIGN PATENT DOCUMENTS

| | | | |
|---|---|---|---|
| 2007700 | 11/1970 | Fed. Rep. of Germany . | |
| 2441621 | 3/1976 | Fed. Rep. of Germany . | |
| 2545338 | 4/1976 | Fed. Rep. of Germany | 568/764 |
| 0114509 | 7/1982 | Japan | 514/912 |
| 0139509 | 7/1985 | Japan | 514/912 |

OTHER PUBLICATIONS

The Condensed Eighth Ed Chemical Dictionary, Revised by Hawley, Reinhold Co., New York, 1971 pp. 104, 105, 771, 780.

Merck Index, Eighth Ed, Stecher, editor, Published by Merck & Co., Inc. Rahway, N.J., U.S.A. 1968 pp. 59, 929, 930, 943.

Primary Examiner—Werren B. Lone
Attorney, Agent, or Firm—Jacobs & Jacobs

[57] ABSTRACT

Some compounds having the general formula of

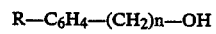

$$R-C_6H_4-(CH_2)_n-OH$$

where we find R is hydrogen, or an alkylic group, possibly mono- or bi-substituted, or a hydroxyl group and n is an entire number varying from 1 to 6.

Such compounds display the common property of being effective against several disorders of the eye (presbiopia, amblyopia, cataract etc.) and may be used as active principles in a pharmaceutical formulation of ophthalmic topical preparations.

14 Claims, No Drawings

PHARMACEUTICAL COMPOUNDS EFFECTIVE AGAINST SEVERAL DISORDERS OF THE EYE IN PARTICULAR THE CATARACT AND COMPOSITION CONTAINING THEM

The invention relates to a class of chemical products which appear to be efficacious as active principles for prevention and treatment of various types of disorders of the eye and to their utilization in pharmaceutical compositions to be used in ophthalmic topical preparations.

The class of compounds usable as active principles against these disorders can be represented by the following general formula:

$$R-C_6H_4-(CH_2)_n-OH$$

where R is hydrogen, or an alkylic group having from 1 to 6 carbon atoms, or an amminic group possibly mono or bi-substituted, or a hydroxyl group and "n" is an entire number which can vary from 1 to 6.

Such compounds show properties which are especially efficacious to protect the —SH groups from oxidation to —S—S— bonds caused by oxidants, to protect protein structure from the unfolding (denaturing) effect of physical or chemical insults, and to stabilize membranes.

The reported properties of such compounds account for the possible beneficial effects on conditions where a free radical mechanism is supposed.

In fact, degenerative disorders such as cataract is nowadays ascribed fundamentally to three mechanisms i.e. oxidation of structural proteins leading to formation of insoluble aggregates, unfolding (denaturation) of lens proteins, decreased impermeability of lens membranes.

Studies have been conducted to determine the role of —SH oxidation on cataract formation and to devise methods to determine the oxidant activity of biological liquids (serum, saliva, urine etc.).

Consequently, drugs have been tested on such oxidant activity predicting to a possible application for the prevention and treatment of experimental cataracts in animals as well as in human cataracts of various types.

A method of determing the potential therapeutic activity of the drug, based on the reducing effect it gives on the Oxidant Activity of Biological Liquids (BLOA) was devised (see Italian Pat. No. 19932/83, Mar. 7, 1983).

The results of this method were obtained from patients to whom the drug was orally administered.

In recent years extensive studies to find drugs able to produce a reduction of BLOA, when orally administered to patients, have been carried out.

It was found that several NSAID, but not all, are able "in vivo" (only 2-3 of them are also effective "in vitro") to reduce the BLOA after oral administration as described in the mentioned patent, and only in some patients (responsive).

Following these studies it was found that only when the BLOA was reduced by at least 20% of the basic value these "responsive" patients had the cataract improved constantly and the biological liquids (saliva, urine) from the patients contained detectable substances, able to reduce the BLOA "in vitro", when extracted, purified and tested by the method described in an other patent (Italian Pat. No. 21398-A/83 June 1, 1983).

The chemical analysis of such substances has brought to the main findings on which this patent is based.

It is likely that such substances are different metabolites of NSAID but sharing a common chemical reactive group which affords their inclusion in one chemical class of products with similar biochemical activities.

It was found that these substances exerted the antioxidant activity on BLOA "invitro" at concentrations as low as $10^{-9}$M, whereas the original NSAIDs, and only few of them (bendazac, indomethacin), where capable of producing such effect at a concentration never lower than $10^{-3}$M.

It is important to point out that no one of such antioxidants has ever been tested and then found to be usable as anti-cataract agent.

To better asses the antioxidant and anticataract properties of the new drugs to be proposed for prevention and treatment of cataract, "in vivo" and "in vitro" experimental trials were conducted. Some of these trials were carried out according to the methods already described in the Italian Pat. No. 20454 A/83. The "in vivo" trails were carried out on two experimental models currently used for such studies.

Radiation cataract was produced according to a well standardized method widely confirmed by an enormous literature. Two trials using ten rabbits each with both eyes irradiated and only one treated gave 100% protection against the cataract which occurred after three months from the irradiation in 80% of untreated eyes.

Experimental uveitis cataract, which usually starts in 50% of the rabbit eyes after 60 days from the intravenous injection of 0.1 ml horse serum was also used as "in vivo" model of experimental cataract. In one trial twelve rabbits were used. Both eyes were injected and one was topically treated with the ophthalmic preparation.

Full protection was observed in 100% of cases up to 6 months from the beginning of the treatment, which was started right after the serum injection into the vitreous body.

In both "in vivo" trials the compounds A were used at a concentration of 0.05% in the opthalmic preparation.

A proper application of two drops to the eyes (keeping the eyelids forcibly open for two minutes during and after the application) was carried out three times a day.

In the "in vitro" experiments the compounds A were compared to other drugs already known as putative anticataract drugs. In TABLE 1 these compounds are expressed by the letters a, b, c, d and e.

It was found that the break-down products of NSAID obtained by "in vivo" metabolization in "responsive" humans and rats, those obtained by perchloration, which will be described later in the text, and those commercially available and previously purified by chemical procedures showed similar chemical structure.

The chemical structure, consisting in a hydroxyl group bound to a benzene ring by an alkylic chain of variable length, was recognized in all such compounds which showed antioxidant and anticataract properties as previously reported.

In particular, the compounds benzyl-alcohol, m-hydroxy-metylaniline and m-hydroxy-benzyl-alcohol were identified. They showed similar if not identical properties so that they were included in an unitary group A, as reported in the following specification.

It is important to bring to the attention of the reader the fact that these compounds, even though chemically known, have never been used as active principles in ophthalmic preparations. However in the light of a large and recent literature, these compounds show properties [antioxidant effects, effect on membrane fluidity, opposite stimulating and inhibitory dose-dependent effect on ($Na^+-K^+$) ATPase protein antidenaturant effect at low ($10^{-6}$M) concentration] that can allow us to define them as vitamin E analogues.

Vit. E has been successfully used "in vitro" models resembling eye disorders attributed to oxidative insult caused by free radicals.

However no evidence has been given of its utility for medical treatment of ocular pathological conditions due perhaps to its failure to reach therapeutic concentrations within the eye. For the same reason topical application of Vit. E was never tested nor investigated.

Thus regarding the possible beneficial use of these compounds as free radical scavengers in eye pathology the following advantages over Vit. E must be pointed out:

(1) easy penetration into the inner eye against lack of penetration of Vit. E, due to lower M.W. and well balanced hydro- and lipo-solubility;

(2) very high specific activity as antioxidants and membrane stabilizers (active bioavailable concentration between $10^{-6}$M and $10^{-8}$M) lower toxicity;

(3) mild anti-inflammatory activity;

(4) enzyme stimulating effects.

Therefore the therapeutic activity of these compounds could be easily anticipated as obvious and highly predictable due to the evidence that the majority of laboratory work has been carried out on blood red cells which are very similar to the lens in respect to environmental and metabolic conditions.

In TABLE 1 we show the results of BLOA of the compounds listed below by the following legend:

Blood serum mixed with:

(a) hydroxy-methyl-aniline;

(b) hydroxy-methyl-indazalone;

(c) 2(2-fluor-3'-4'dihydroxy-4-4 diphenyl)propionic acid;

(d) benzidamine and bendaline.

It is worth mentioning that:

The presence of a primary alcoholic hydroxyl bound to a benzene ring through a methylic bridge, and the concentration in biological liquids extremely low (about one millionth part in weight of the original NSAID administered to responsive patient) are two very important features.

The common chemical general formula reported before, representative of such compounds, was determined by the following preparative and analytic procedures:

the method to determine the BLOA (Biological Liquid Oxidant Activity) reported in the patent filed in 1983.

Extraction of biological liquids (saliva, urine, tears) by means of organic solvent (hexane, methanol, ethylacetone, benzene, chloroform etc. etc.) reported in a previous patent No. 21398-A/83, June 1, 1983.

Thin layer chromotography on silica gel and columnchromatography.

Mass spectrometry

Nuclear magnetic resonance

Infra-red spectroscopy

Ultra-violet spectroscopy.

Beside the BLOA test, the demonstration that the extracted substances were identical with the supposed NSAID metabolites responsible for the anticataract effect in responsive patients was given by the finding that the topical application to the eye produced the same clinical effect given by the original NSAID.

Moreover the same substances found in rats and rabbits treated with NSAID could be produced "in vitro" by perchloric acid as described hereafter:

The NSAID at a concentration of 0.1 percent in distilled water is mixed in a glass vessel with 0.1N perchloric acid.

Concentrations between 0.05 and 0.3N perchloric acid have been used but without changing the volume ratio between NSAID and perchloric acid which was always 1 ml NSAID solution and 0.1 ml perchloric acid.

The mixture was incubated at temperature ranging from 0° to 37° C. for a time ranging from 15 to 90 minutes. The optimum conditions were found to be 0.05N perchloric acid, 15–20 min. incubations and 18° C. where NSAID sample was 1 ml 0.1%.

Then the antioxidant substances produced in the incubation mixtures were extracted and analyzed according to the previously listed procedures.

The products so obtained were found to be identical with those obtained by "in vivo" metabolization of NSAID in "responsive" human or rats.

The results shown in TABLE 1 indicate that the antioxidant activity on BLOA of compounds of group A is evident at concentrations ranging from $10^{-3}$M to $10^{-9}$M.

On the contrary among the other tested compounds (a, b, c, d and e) only compound a showed a remarkable anti-BLOA effect at concentration of $10^{-8}$M whereas Bendaline shows anti-BLOA effect at concentration of $10^{-3}$M whereas Benzidamine has no effect at all.

The effect of these compounds on heat induced cataract on isolated entire bovine lenses kept at 55° C. in standardized conditions (pH, ionic strengt, incubation time, light exposure etc. etc.) is reported in TABLE 2, where the signes +,— and n.d. indicate protection, cataract and undetermined, respectively.

It is evident that Bendaline and Benzidamine (as other tested NSAIDs as indoprofen, phenyl-butazone, aspirin) show an aspecific protection at concentration of not less than $10^{-3}$M.

On the other hand the compounds A show protection at concentrations ranging from $10^{-6}$M to $10^{-8}$M, whereas $10^{-2}$M an opposite effect (cataractogenic) is apparent.

These dose-dependent opposite effects can be explained as it has been shown on red blood cells, by the activity on membrane fluidity, increased at high concentration leading to membrane fusion but stabilized by lower concentrations.

Such concentration also produces stimulation of ($Na^+-K^+$) ATPase.

It is then apparent that the antioxidant and membrane stabilizing effects are not related since antioxidation occurs at the concentration of $10^{-3}$ which does not allow protection of membrane integrity.

A third "in vitro" experiment showing the protective effect against oxidative insult to the lens "in vitro" is reported here:

In rabbit lenses cultured for 3 h in Krebs-Ringer bicarbonate-glucose medium (KRB) alone, malondialdeyde (MDA) was 1.18±0.14 μmole/g, (mean S.D.

n=3). MDA was higher (P<001), 4.05±0.13 μmole/g, n=3 in lenses exposted to reactive species of $O_2$ generated by the xantine-xantine-oxidase-$Fe^{3+}$.

ADP system in the absence of benzyl-alcohol and was 2.15±0.15 μmole/g, n=3 in the presence of 1 mM benzyl-alcohol, showing its protective effect against lipid peroxidative damage to the lens.

Similarly, benzyl-alcohol also prevented lenticular thiol oxidation.

Reduced glutathione was 7.46±0.44 μmole/g, n=3 in lenses cultured in KRB medium alone, 1.34±0.27 μmole/g, n=3 and 2.63±0.16 μmole/g, n=3 in lenses subjected to oxidative stress in the absence and presence of 1 mM benzyl-alcohol, respectively.

The experimental evidence demostrates that benzyl-alcohol is a potent antioxidant suitable for clinical trials in the human.

The reported compounds have been found suitable for topical application to the eye.

The ocular bioavailability and efficacy of these compounds are dependent on the following characteristics:

(1) They are able to reduce the oxidant activity of biological liquids(BLOA) at a very low concentration ($10^{-9}$); this finding has been shown by means of a specific reagent represented by lens homogenate from bovine lenses and described in the Italian Pat. No. 1932A/83, now also granted in USA.

(2) The optimum concentration of these compounds is $5 \times 10^{-3}$M in the drop preparation as compared to other substances also able to reduce the oxidant activity at a much higher concentration but that can produce ADR as ichting and redness responsible for lack of compliance and patient dropout.

(3) The molecular weight of these antioxidants must be lower than 400 because larger molecules can hardly penetrate the eye when topically applied.

(4) Either lipo- and hydro-solubility are important chemical features of such compounds to allow them to penetrate the corneal tear film and the epithelium layer of the cornea in order to reach the inner tissues within the eyeball.

(5) The compounds show a retention factor (RF) in the order of 0.025 when analyzed by TLC under specific technical conditions and eluent composition.

Besides the clinical data reported in TABLE 3, it is worth mentioning the proposed clinical effects of the compounds A:

full prevention of human an animal (dog, horse) cataract when applied continously especially in individuals at risk (trauma, eye surgery, diabetes, steroid treatment, family history of cataract ecc.);

prevention and treatment of eye visual conditions other than cataract in supposedly functional visual losses as presbiopia, amblyopia;

treatment and prevention of other organic visual disorders as keratoconus, macular degeneration or chronic blepharoconjuntivites, uveites and chronic inflammation of the outer eye (lacrimal gland, scleritis);

prevention of experimental retrolental fibroplasia as shown by experimental work on kittens under high oxygen atmosphere;

protection against photic or UV injury of lens and retina and X-ray irradiation;

protection against cataractogenic effect of antiglaucoma topical drugs;

protection of lens and retina before or after microsurgery during vitrectomy, laser treatment, glaucoma and retinal detachment surgery;

treatment of optic neuritis;

treatment and prevention of retinal myopic or senile degenerations;

in general all degenerative and senile disorders of the eye where an oxidative insult is advocated as on possible etiological factor;

senile and myopic liquefaction and degeneration of vitreous body;

the duration of treatment to achieve a remarkable and appreciable visual improvement is very short (2-3 week) even though it is obviously highly dependent on the severity of the pathologic condition to be treated;

compliance was almost 100% with no ocular side effects and no general or local adverse drug reactions. Eye drops formulation. Excipients=they are usually the same found in artificial tears i.e.:

Methylcellulose 0.1 g. to 0.3 g %
Sodium chloride 0.75 g. %
Potassium chloride 0.15 g. %
EDTA Sodium salt 0.05 g. %
Distilled water to 100 cc.

Liposolubility must be a fundamental characteristic of the anticataract agents as to allow their easy penetration into the eye through the cornea.

It is worth reminding that all above reported data refer to the specific preventive and curative activity of such a class of compounds for diseases of different ethiological causes.

However other ocular conditions as conjuntivites, uveitis, chronic inflammations, macular myopic or senile degeration, myopia, keratoconus and similar degenerative ocular patology can benefit from this treatment.

For the topical application the compounds reported in this invention are formulated for topical eye drops in acqueous solutions also usable for subcnjunctival injections.

The solution must be isotonic with tears and contain concentration of the compunds from 0.01 g to 2 g every 100 ml. of solution, containing also the other salts and preservatives which however should be compatible with the active principle in order that stability and efficacy are ensured. TABLE 4 shows the striking effect of these Compounds on Amblyopia.

It is evident that topical treatment produces significant improvement of visual acuity in amblyopic eyes previously treated without succes with conventional eye patching.

Either strabismic or anisometropic amblyopias appear to respond to the treatment provided a proper application is carried out using also patching of the good eye during the treatment which requires a short time (one month is sufficient) to produce the improvement of visual acuity.

The last example relates to a double blind clinical trial versus placebo carried out on ten male volunteers aged 45 with 1 dyopter hyperopia to whom the eye drops were applied to test a possible preventive effect on presbiopia.

They were carefully selected into a homogeneous group i.e. healty with no general or ocular treatments, similar working activity requiring the best near vision, full compliance to the trial to be carried on for three years.

The effectiveness criteria were the change of refractive error and the extend of glass correction for near vision (expressed by clear reading without strain of the smallest characters of the near vision chart) at 25 cm.

distance from each eye separately, under standardized conditions of illumination, ocular rest, pupil size.

Two drops were applied twice a day in both eyes for three years.

Eye examination was carried out every six months.

After three years continous tratment refractive error increased by +0.405±0.092 (S.D) and glass correction for near was +2.514±0.15 (S.D) in five subjects treated with placebo whereas they were +0.392±0.12 (S.D) and 1.450±0.15 (S.D) in the remaining subjects treated with drops containing compounds A respectively.

Visual acuity was unchanged as all other ocular parameters.

The difference of glass corrections for near between placebo and compounds A treated eyes is highly significant ($P < 0.001$).

No difference of hyperopia before and after treatment was found.

These results indicate that compounds A are very efficacious in preventing loss of accomodation (presbiopia).

This effect might be ascribed to an increased membrane fluidity of the lens causing maintainance of lens plsticity responsible for the lens deformation occurring during static accomodation.

Other mechanisme as described refractive index of the cortex, inhibition of lens growth or prevention of shape or lens curvature changes are not consistent with the clinical findings.

TABLE 1

| Concentration of Compounds | BLOA decrease (expressed as percent decrease of - SH groups) | | | | | |
|---|---|---|---|---|---|---|
| | a | b | c | d | e | Group A |
| $10^{-3}$ M | 15 | 20 | 20 | 29 | 21 | 20 |
| $10^{-4}$ M | 20 | 20 | 21 | 30 | 30 | 20 |
| $10^{-5}$ M | 19 | 21 | 22 | 30 | 30 | 20 |
| $10^{-6}$ M | 20 | 24 | 29 | | | 20 |
| $10^{-7}$ M | 20 | 30 | 28 | | | 20 |
| $10^{-8}$ M | 20 | 28 | 28 | | | 20 |
| $10^{-9}$ M | 32 | 29 | 27 | | | 20 |
| Basal value (no compound added) | 31 | 31 | 27 | 30 | 30 | 30 |

TABLE 2

| COMPOUNDS | MOLAR CONCENTRATION IN TCC 199 SOLUTION | | | | | | |
|---|---|---|---|---|---|---|---|
| | $10^{-3}$ | $10^{-4}$ | $10^{-5}$ | $10^{-6}$ | $10^{-7}$ | $10^{-8}$ | $10^{-9}$ |
| 2-hydroxy-methyl-anilin | − | − | − | + | + | + | − |
| hydroxy-methyl-indazolone | + | + | + | ± | − | − | − |
| 2-(2-fluor-3',4'-dihydroxy-4 diphenyl) propionic acid | + | + | + | + | − | − | − |
| benzidamine | + | − | − | n.d. | n.d. | n.d. | n.d. |
| bendaline | + | − | − | n.d. | n.d. | n.d. | n.d. |
| control | − | − | − | − | − | − | − |
| Group A | − | − | − | + | + | + | + |

TABLE 3

| Sex | Age | Eye | I Examination Visus | Refraction spher. | Cyl. | Catar | Days treat. | Eye | II Examination Visus | Refraction spher. | Cyl. | Days treat. | Clinical Judgement |
|---|---|---|---|---|---|---|---|---|---|---|---|---|---|
| F | 59 | R | 0,001 | | | T | 30 | R | 0,001 | | | 30 | + |
| | | L | 0,5 | | | C | | L | 0,8 | | −0,50 | | |
| F | 73 | R | 0,2 | | | C | 60 | R | 0,2 | +0,50 | | 60 | + |
| | | L | 0,5 | | | C | | L | 0,6 | | +0,50 | | |
| F | 80 | R | 0,2 | | | C | 90 | R | 0,4 | | | 90 | + |
| | | L | 0,3 | | | C | | L | 0,5 | | | | |
| F | 77 | R | 1,0 | +4 | | C | 30 | R | 0,9 | +4 | | 30 | + |
| | | L | 0,1 | +3 | | C | | L | 0,4 | +1 | +0,50 | | |
| F | 72 | R | 0,2 | +2 | +2 | C | 30 | R | 0,4 | +4,50 | +1,50 | 30 | + |
| | | L | 0,3 | +2 | +2,50 | C | | L | 0,4 | +2,50 | +2,50 | | |
| F | 85 | R | | | | T | 60 | R | | | | 60 | + |
| | | L | 0,2 | −1,50 | −0,50 | C | | L | 0,5 | −1,50 | −0,50 | | |
| F | 77 | R | 0,083 | | | C | 30 | R | 0,4 | | | 30 | + |
| | | L | 0,2 | | | C | | L | 0,6 | | | | |
| M | 63 | R | 0,6 | −4 | −1 | C | 30 | R | 0,7 | −4,50 | −1 | 30 | + |
| | | L | 0,3 | −4 | −1,50 | C | | L | 0,5 | −4,50 | −1,50 | | |
| M | 70 | R | 1,1 | +1,50 | | C | 30 | R | 1,2 | | +0,50 | 30 | + |
| | | L | 0,9 | +1,50 | +0,50 | C | | L | 1,2 | +0,50 | | | |
| F | 64 | R | 0,3 | +0,75 | | C | 30 | R | 0,5 | +0,75 | | 30 | + |
| | | L | 0,8 | +0,50 | | C | | L | 0,1 | +0,50 | | | |
| M | 65 | R | 0,7 | −6 | | SC | 60 | R | 0,8 | −6 | | 60 | + |
| | | L | | | | A | | L | | | | | |
| M | 67 | R | 0,083 | −18 | | SC | 60 | R | 0,3 | −18 | | 60 | + |
| | | L | 0,083 | −17 | | SC | | L | 0,2 | −17 | | | |
| M | 70 | R | 0,3 | −0,25 | −0,75 | SC | 30 | R | 0,4 | −0,25 | −0,50 | 30 | + |
| | | L | 0,7 | +1 | +0,50 | SC | | L | 0,9 | +0,50 | +0,50 | | |
| F | 46 | R | 1,5 | | | TR | 60 | R | 1,5 | | | 60 | + |
| | | L | 0,6 | −4 | | SC | | L | 0,9 | −3 | −0,50 | | |
| F | 52 | R | 0,6 | | | SC | 60 | R | 1,5 | +1 | | 60 | + |
| | | L | | | | A | | L | | | | | |
| F | 60 | R | 0,2 | −20 | −0,75 | SC | 60 | R | 0,3 | −20 | −1,25 | 60 | + |
| | | L | 0,4 | −16 | −0,75 | SC | | L | 0,5 | −18 | −1,50 | | |
| F | 55 | R | 1,1 | | | SC | 24 | R | 1,5 | | | 24 | + |
| | | L | 0,6 | −1 | | SC | | L | 1,0 | −1 | | | |
| M | 53 | R | 1,4 | −0,75 | | SC | 60 | R | 1,4 | +0,50 | | 60 | + |
| | | L | 0,4 | +0,50 | | SC | | L | 0,6 | | −0,50 | | |
| M | 43 | R | 1,5 | | +0,50 | SC | 120 | R | 1,5 | | +0,50 | 150 | + |
| | | L | 0,8 | | | SC | | L | 1,2 | −1,25 | | | |
| M | 68 | R | 0,8 | +0,50 | +1 | SC | 60 | R | 1,2 | +0,50 | +1 | 60 | + |

TABLE 3-continued

| | | | | I Examination | | | | | | II Examination | | | |
| | | | | Refraction | | | Days | | | Refraction | | Days | Clinical |
| Sex | Age | Eye | Visus | spher. | Cyl. | Catar | treat. | Eye | Visus | spher. | Cyl. | treat. | Judgement |
|---|---|---|---|---|---|---|---|---|---|---|---|---|---|
| | | L | 0,4 | +1 | +0,50 | SC | | L | 0,5 | +1 | | | |

F = Female
M = Male
C = Cortical
SC = Sub-capsular
A = Aphakic
T = Transparent

Only cataract patients, in whom the progression of the cataract had been preliminarily determined in a 6 months follow up, were admitted to the trial. These patients were followed up for one year and no change of cataract was observed. Ten patients used as control with only placebo were examined at the same time. No one of the treated patients underwent cataract extraction whereas 60% of the placebo group did. No one of this group showed any improvement during one year follow up.

TABLE 4
AMBLYOPIA BY ANISOMETROPIA
SUMMARY OF CLINICAL FINDINGS
BEFORE AND AFTER TREATMENT WITH BENZYL.A.COLLYRIUM

| Case N. | Age | Sex | Eye | Visual acuity | | | Daily occlusion | Overall clinical |
| | | | | Before | 30 days | 60 days | hrs. | assessment |
|---|---|---|---|---|---|---|---|---|
| 1 | 11 | M | R | 0.3 | 0.7 | 0.8 | 4 | IMPROVEMENT |
| 2 | 19 | F | R | 0.3 | 0.6 | 0.8 | 4 | IMPROVEMENT |
| 3 | 13 | M | L | 0.3 | 0.8 | 0.8 | 24 | IMPROVEMENT |
| 4 | 20 | M | R | 0.3 | 0.6 | 0.9 | 4 | IMPROVEMENT |
| 5 | 19 | F | L | 0.3 | 0.8 | 0.8 | 4 | IMPROVEMENT |
| 6 | 18 | F | L | 0.4 | 0.7 | 0.8 | 24 | IMPROVEMENT |
| 7 | 12 | F | R | 0.2 | 0.7 | 0.9 | 4 | IMPROVEMENT |
| 8 | 12 | F | L | 0.2 | 0.7 | 1.0 | 4 | IMPROVEMENT |
| 9 | 11 | F | R | 0.4 | 1.1 | 1.0 | 4 | IMPROVEMENT |
| 10 | 13 | M | L | 0.3 | 1.0 | 1.0 | 4 | IMPROVEMENT |
| 11 | 16 | F | R | 0.2 | 0.7 | 0.9 | 4 | IMPROVEMENT |
| 12 | 13 | M | L | 0.3 | 0.9 | 0.8 | 24 | IMPROVEMENT |
| 13 | 19 | F | R | 0.4 | 0.7 | 0.7 | 4 | IMPROVEMENT |
| 14 | 11 | M | L | 0.3 | 1.0 | 0.9 | 4 | IMPROVEMENT |
| 15 | 15 | F | R | 0.2 | 0.7 | 0.8 | 24 | IMPROVEMENT |
| 16 | 18 | F | L | 0.3 | 0.6 | 0.8 | 4 | IMPROVEMENT |
| 17 | 13 | M | L | 0.4 | 1.0 | 0.9 | 4 | IMPROVEMENT |
| 18 | 18 | F | R | 0.3 | 0.8 | 0.9 | 24 | IMPROVEMENT |
| 19 | 15 | F | L | 0.3 | 1.0 | 1.1 | 4 | IMPROVEMENT |
| | | | | | $t = 14.44$ | $t = 19.26$ | | |
| | | | | | $P < 0.001$ | $P < 0.001$ | | |
| 1 | 11 | M | R | 0.4 | 0.8 | 0.8 | 4 | IMPROVEMENT |
| 2 | 12 | M | R | 0.3 | 0.7 | 0.8 | 4 | IMPROVEMENT |
| 3 | 8 | F | L | 0.4 | 0.7 | 0.7 | 24 | IMPROVEMENT |
| 4 | 8 | F | L | 0.3 | 0.8 | 0.8 | 4 | IMPROVEMENT |
| 5 | 9 | F | L | 0.4 | 1.0 | 1.0 | 4 | IMPROVEMENT |
| 6 | 10 | F | R | 0.3 | 0.6 | 0.6 | 4 | IMPROVEMENT |
| 7 | 11 | M | L | 0.3 | 0.8 | 0.8 | 4 | IMPROVEMENT |
| 8 | 6 | F | R | 0.3 | 1.0 | 1.0 | 4 | IMPROVEMENT |
| 9 | 8 | F | R | 0.3 | 0.8 | 0.7 | 4 | IMPROVEMENT |
| 10 | 9 | F | R | 0.4 | 0.6 | 0.7 | 4 | SLIGHT IMPROV. |
| 11 | 9 | M | R | 0.2 | 0.4 | 0.4 | 4 | SLIGHT IMPROV. |
| | | | | | $t = 8.96$ | $t = 9.63$ | | |
| | | | | | $P < 0.001$ | $P < 0.001$ | | |

Statistical analysis were analysed by means of Student's t-test for paired data

I claim:

1. A method for the treatment of cataracts of the eye in humans and animals, which comprises topically administering to the eye of a human or animal in need thereof an anti-cataract effective amount of a compound of the formula

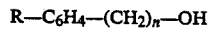

R—C$_6$H$_4$—(CH$_2$)$_n$—OH wherein R is hydrogen, alkyl of 1 to 6 carbon atoms, amino, monosubstituted amino, disubstituted amino, or hydroxyl, and n is a whole number of from 1 to 6.

2. The method according to claim 1, wherein said compound is benzyl alcohol.

3. The method according to claim 1, wherein said compound is m-hydroxybenzyl alcohol.

4. The method according to claim 1, wherein said compound is m-hydroxybenzyl aniline.

5. A pharmaceutical composition for the treatment of cataracts of the eye in humans and animals in the form of eyedrops comprising an aqueous solution comprising an anti-cataract effective amount of a compound of the formula

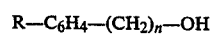

R—C$_6$H$_4$—(CH$_2$)$_n$—OH wherein R is hydrogen, alkyl of 1 to 6 carbon atoms, amino, monosubstituted amino, disubstituted amino, or hydroxyl, and n is a whole number of from 1 to 6, the concentration of said compound in said aqueous solution being less than $10^{-2}$M.

6. The composition according to claim 5, wherein said composition is isotonic with tears.

7. The composition according to claim 5, wherein said compound is benzyl alcohol.

8. The composition according to claim 5, wherein said compound is m-hydroxybenzyl alcohol.

9. The composition according to claim 5, wherein said compound is m-hydroxybenzyl aniline.

10. A method for the treatment of cataracts of the eye in humans and animals, which comprises topically administering to the eye of a human or animal in need thereof an anti-cataract effective amount of eyedrops comprising an aqueous solution of a compound of the formula $$R—C_6H_4—(CH_2)_n—OH$$

wherein R is hydrogen, alkyl of 1 to 6 carbon atoms, amino, monosubstituted amino, disubstituted amino, or hydroxyl, and n is a whole number of from 1 to 6, the concentration of said compound in said aqueous solution being less than $10^{-2}$M.

11. The method according to claim 10, wherein said eyedrops are isotonic with tears.

12. The method according to claim 10, wherein said compound is benzyl alcohol.

13. The method according to claim 10, wherein said compound is m-hydroxybenzyl alcohol.

14. The method according to claim 10, wherein said compound is m-hydroxybenzyl aniline.

* * * * *